US009550710B2

(12) United States Patent
Dhepe et al.

(10) Patent No.: US 9,550,710 B2
(45) Date of Patent: Jan. 24, 2017

(54) PROCESS FOR DEPOLYMERIZATION OF LIGNIN

(71) Applicant: Council of Scientific and Industrial Research, New Delhi (IN)

(72) Inventors: Paresh Laxmikant Dhepe, Pune (IN); Ashutosh Anant Kelkar, Pune (IN); Babasaheb Mansub Matsagar, Pune (IN); Sandip Kumar Singh, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 14/890,020

(22) PCT Filed: May 9, 2014

(86) PCT No.: PCT/IN2014/000320
§ 371 (c)(1),
(2) Date: Nov. 9, 2015

(87) PCT Pub. No.: WO2014/181360
PCT Pub. Date: Nov. 13, 2014

(65) Prior Publication Data
US 2016/0168062 A1 Jun. 16, 2016

(30) Foreign Application Priority Data
May 9, 2013 (IN) .......................... 1387/DEL/2013

(51) Int. Cl.
| C07C 69/00 | (2006.01) |
| C07C 37/00 | (2006.01) |
| C07G 1/00 | (2011.01) |
| C08J 11/26 | (2006.01) |
| B01J 31/02 | (2006.01) |
| C07C 1/20 | (2006.01) |
| C07C 29/00 | (2006.01) |
| C07C 29/86 | (2006.01) |
| C07C 29/94 | (2006.01) |
| C07C 37/72 | (2006.01) |
| C07C 37/88 | (2006.01) |
| C07C 41/01 | (2006.01) |
| C07C 41/38 | (2006.01) |
| C07C 41/46 | (2006.01) |
| C07C 45/00 | (2006.01) |
| C07C 45/80 | (2006.01) |
| C07C 45/86 | (2006.01) |
| C07C 51/00 | (2006.01) |
| C07C 51/48 | (2006.01) |
| C07C 51/50 | (2006.01) |
| C07C 67/00 | (2006.01) |
| C07C 67/58 | (2006.01) |
| C07C 67/62 | (2006.01) |
| C07C 27/00 | (2006.01) |

(52) U.S. Cl.
CPC .......... *C07C 37/004* (2013.01); *B01J 31/0217* (2013.01); *B01J 31/0282* (2013.01); *B01J 31/0285* (2013.01); *C07C 1/20* (2013.01); *C07C 27/00* (2013.01); *C07C 29/00* (2013.01); *C07C 29/86* (2013.01); *C07C 29/94* (2013.01); *C07C 37/72* (2013.01); *C07C 37/88* (2013.01); *C07C 41/01* (2013.01); *C07C 41/38* (2013.01); *C07C 41/46* (2013.01); *C07C 45/00* (2013.01); *C07C 45/80* (2013.01); *C07C 45/86* (2013.01); *C07C 51/00* (2013.01); *C07C 51/48* (2013.01); *C07C 51/50* (2013.01); *C07C 67/00* (2013.01); *C07C 67/58* (2013.01); *C07C 67/62* (2013.01); *C07G 1/00* (2013.01); *C08J 11/26* (2013.01); *C07C 2531/02* (2013.01); *C08J 2397/00* (2013.01); *Y02W 30/706* (2015.05)

(58) Field of Classification Search
CPC . B01J 31/0217; B01J 31/0282; B01J 31/0285; C07C 1/20; C07C 2531/02; C07C 29/00; C07C 29/86; C07C 29/94; C07C 37/004; C07C 37/72; C07C 37/88; C07C 41/01; C07C 41/38; C07C 41/46; C07C 45/00; C07C 45/80; C07C 45/86; C07C 51/00; C07C 51/48; C07C 51/50; C07C 67/00; C07C 67/58; C07C 67/62; C07G 1/00; C08J 11/26; C08J 2397/00; Y02W 30/706
See application file for complete search history.

(56) References Cited

FOREIGN PATENT DOCUMENTS

| CN | 102321251 | * | 1/2012 |
| CN | 102321251 A | | 1/2012 |
| CN | 102924204 A | | 2/2013 |
| WO | WO-2014/181360 | | 11/2014 |

OTHER PUBLICATIONS

George et al. (The effect of ionic liquid cation and anion combinations on the macromolecular structure of lignins, Green Chemistry, 13, 3375-3385, 2011).*
Written opinion for PCT/IN2014/000320, 2014.*
International Application No. PCT/IN2014/000320, International Search Report and Written Opinion mailed Sep. 29, 2014, 7 pgs.
Cox, Blair J., et al., "Depolymerization of oak wood lignin under mild conditions using the acidic ionic liquid 1-H-3-methylimidazolium chloride as both solvent and catalyst", *Bioresource Technology*, 118, (2012), 584-588.
Delahaye, Emilie, et al., "Silica ionogels for proton transport", *J. Mater. Chem.*, 22, (2012), 17140-17146.

(Continued)

*Primary Examiner* — Yevegeny Valenrod
*Assistant Examiner* — Blaine G Doletski
(74) *Attorney, Agent, or Firm* — Schwegman Lundberg & Woessner, P.A.

(57) ABSTRACT

The present invention discloses a process for depolymerization of lignin to yield substituted phenolic monomers using Brönsted ionic liquid as catalyst under mild reaction conditions to obtain an overall yield of monomers up to 97%.

9 Claims, 1 Drawing Sheet

(56) References Cited

OTHER PUBLICATIONS

George, Anthe, et al., "The effect of ionic liquid cation and anion combinations on the macromolecular structure of lignins", *Green Chem.*, 13, (2011), 3375-3385.

Jia, Songyan, et al., "Cleaving the β-O-4 Bonds of Lignin Model Compounds in an Acidic Ionic Liquid, 1-H-3-Methylimidazolium Chloride: An Optional Strategy for the Degradation of Lignin", *ChemSusChem*, 3(9), (2010), 1078-1084.

Reichert, Elena, et al., "Electro-catalytic oxidative cleavage of lignin in a protic ionic liquid", *Physical Chemistry Chemical Physics*, 14(15), (2012), 5214-5221.

Stärk, Kerstin, et al., "Oxidative Depolymerization of Lignin in Ionic Liquids", *ChemSusChem*, 3, (2010), 719-723.

Yan, Ning, et al., "Hydrodeoxygenation of Lignin-Derived Phenols into Alkanes by Using Nanoparticle Catalysts Combined with Brønsted Acidic Ionic Liquids", *Angew. Chem. Int. Ed.*, 49, (2010), 5549-5553.

\* cited by examiner

Fig: 1
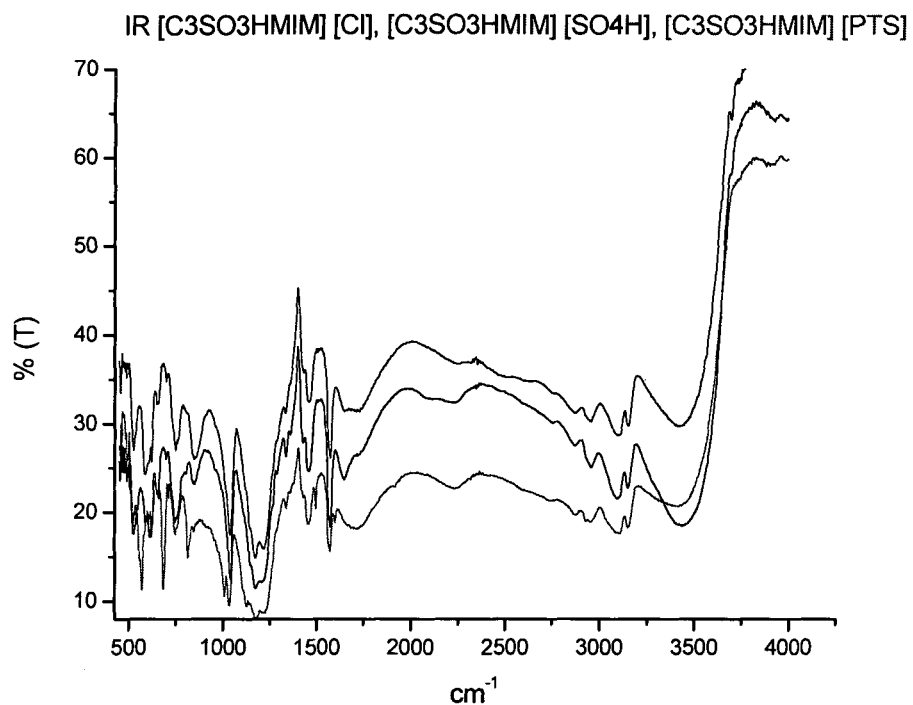
Fig: 2
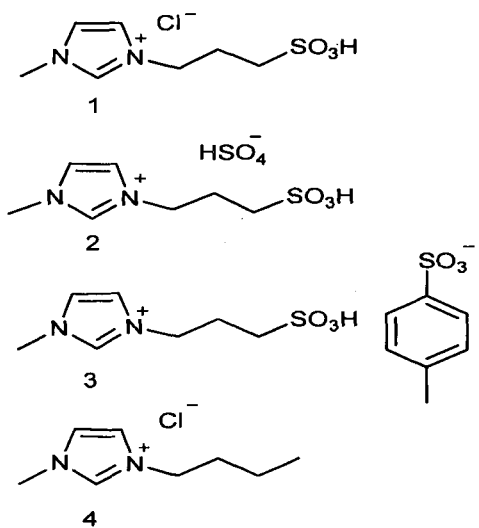

PROCESS FOR DEPOLYMERIZATION OF LIGNIN

PRIORITY CLAIM TO RELATED APPLICATIONS

This application is a U.S. national stage application filed under 35 U.S.C. §371 from International Application Serial No. PCT/IN2014/000320, which was filed 9 May 2014, and published as WO2014/181360 on 13 Nov. 2014, and which claims priority to India Application No. 1387/DEL/2013, filed 9 May 2013, which applications and publication are incorporated by reference as if reproduced herein and made a part hereof in their entirety, and the benefit of priority of each of which is claimed herein.

FIELD OF THE INVENTION

The present invention relates to a process for depolymerization of lignin to obtain substituted phenolic monomers with molecular weight less than 300 using acidic ionic liquids as catalyst under mild reaction conditions to obtain an overall yield of monomers up to 97%.

BACKGROUND AND PRIOR ART

Lignin is a complex polymer made up of several aromatic rings linked together via C—C bond or C—O—C bonds (FIG. 1). Lignin is present in lignocellulosic materials with varying quantities (15-25%) depending upon the plant species, growth conditions etc. Upon depolymerisation, lignin can yield several aromatic monomers which can be used as fuel additives and platform chemicals. Generally, there are five categories of the chemical depolymerization of lignins reported in the prior art which includes (1) base-catalyzed, (2) acid-catalyzed, (3) metallic catalyzed, (4) ionic liquids-assisted, and (5) supercritical fluids-assisted lignin depolymerizations.

Article titled, "Depolymerization of oak wood lignin under mild conditions using the acidic ionic liquid 1-H-3-methylimidazolium chloride as both solvent and catalyst" by Blair J. Cox, John G. Ekerdt in Bioresource Technology 118 (2012) 584-588 reports the Oak wood lignin, which was separated from the wood using dissolution in the ionic liquid 1-methyl-3-ethylimidazoliumacetate and subsequent precipitation, was successfully depolymerized in the acidic ionic liquid 1-H-3-methylimidazolium chloride under mild conditions (110-150° C.). Based on gel permeation chromatography results, an increase in temperature from 110 to 150° C. increased the rate of reaction, but did not significantly change the final size of the lignin fragments.

Article titled, "Electro-catalytic oxidative cleavage of lignin in a protic ionic liquid" by Elena Reichert, Reiner Wintringer, Dietrich A. Volmerb and Rolf Hempelmann in Phys. Chem. Chem. Phys., 2012, 14, 5214-5221 reports a new approach of electro-oxidative cleavage of lignin, dissolved in a special protic ionic liquid, using an anode with particular electro-catalytic activity.

Article titled, "The effect of ionic liquid cation and anion combinations on the macromolecular structure of lignins" by Anthe George, Kim Tran, Trevor J. Morgan, Peter I. Benke, Cesar Berrueco, Esther Lorente, Ben C. Wu, Jay D. Keasling, Blake A. Simmons and Bradley M. Holmes in Green Chem., 2011, 13, 3375-3385 reports that sulfates>lactate>acetate>chlorides>phosphates in terms of the relative impact on reducing lignin molecular weight, with evidence of different anions causing cleavage of different linkages within the lignin. Of the ILs studied, sulfate based ionic liquids most comprehensively broke down the largest lignin molecules, resulting in fragments>1000-3000 u (by polysaccharide calibration). The lactate anion, while appearing less capable of breaking down the largest lignin molecules, causes the formation of significant quantities of the smallest sized fragments observed (2000-500 u).

Article titled, "Cleaving the (B—O-4) Bonds of Lignin Model Compounds in an Acidic Ionic Liquid, 1-H-3-Methylimidazolium Chloride: An Optional Strategy for the Degradation of Lignin" by Songyan Jia, Blair J. Cox, Xinwen Guo, Z. Conrad Zhang, and John G. Ekerdt in ChemSusChem 2010, 3, 1078-1084 reports The hydrolysis of B—O-4 bonds in two lignin model compounds was studied in an acidic ionic liquid, 1-H-3-methylimidazolium chloride. The B—O-4 bonds of both guaiacylglycerolb-guaiacyl ether and veratrylglycerol-b-guaiacyl ether underwent catalytic hydrolysis to produce guaiacol as the primary product with more than 70% yield at 150° C.

Article titled, "Hydrodeoxygenation of Lignin-Derived Phenols into Alkanes by Using Nanoparticle Catalysts Combined with Brønsted Acidic Ionic Liquids" by Ning Yan, Yuan Yuan, Ryan Dykeman, Yuan Kou, and Paul J. Dyson in Angew. Chem. Int. Ed. 2010, 49, 5549-5553 reports the transformation of lignin-derived phenolic compounds to alkanes has been achieved in ILs. The catalytic system is composed of metal NPs and a functionalized Brønsted acidic IL immobilized in a nonfunctionalized IL, allowing hydrogenation and dehydration reactions to occur in tandem.

Depolymerization of lignin yields products like gases (CO, $H_2$, $CH_4$, alkanes etc.) or substituted phenolic monomer compounds. Depolymerization of lignin using soluble base (NaOH, KOH, CsOH etc.) and using supercritical water is known. However, these methods are not environmentally benign and are energy consuming. Hence it is required to develop a process which will not use soluble base, will operate at milder reaction conditions, and will be environmentally benign. Despite the fact that some ionic liquids are appropriate solvents for lignin dissolution/depolymerization, however, the high cost of the ionic liquids limited their application on large quantity of lignin depolymerization reactions. Therefore, there is need in the art for recylization/recovery of ionic liquids. However, it is reported fact that it is difficult to separate the ionic liquid with lignin-derived molecules because of the π-π interaction between ionic liquid and aromatic moieties. Also, prior art failed to teach an effective method for recylization/recovery of ionic liquids.

OBJECTIVE OF THE INVENTION

The main objective of the present invention is to provide an environmentally benign process for the depolymerization of lignin using acidic ionic liquids as catalysts under mild reaction conditions to yield substituted phenolic compounds with molecular weight<300 in high yields.

Another objective of the invention is to recover/recycle of ionic liquids from the reaction mass of lignin depolymerization.

SUMMARY OF THE INVENTION

Accordingly, the present invention provides a process for the depolymerization of lignin to obtain aromatic products comprising the steps of:

a. adding dealkaline lignin and Brönsted ionic liquid having —$SO_3H$ group in the range of 1:0.25 to 1:1 to a mixture of water and methanol wherein the ratio of methanol to water is in the range of 0:1 to 5:1 to obtain a reaction mixture;

b. stirring the reaction mixture obtained in step (a) at a temperature range of 100 to 170° C. for a period of 0.5 to 6 hrs to afford the aromatic products with 95-97% yield and a mass balance of >90%.

In one embodiment of the present invention the Brönsted ionic liquid having —SO$_3$H group used in step (a) is selected from the group consisting of (1-methyl-3-(3-sulfopropyl)-1H-imidazol-3-ium 4-methylbenzenesulfonate), (1-methyl-3-(3-sulfopropyl)-1H-imidazol-3-ium hydrogensulfate), (1-methyl-3-(3-sulfopropyl)-1H-imidazol-3-ium chloride).

In an embodiment of the present invention the Brönsted ionic liquid having —SO$_3$H group used is (1-methyl-3-(3-sulfopropyl)-1H-imidazol-3-ium hydrogensulfate).

In another embodiment of the present invention the aromatic products are phenolic monomers obtained with m/z in the range of 100 to 300.

Still in another embodiment of the present invention the phenolic monomers are THF soluble.

Still in another embodiment of the present invention the phenolic monomers are selected from the group consisting of 3,5 di ter-butyl,4-methylphenol, 2-ter-butyl,4-methylphenol, 4-acetyl benzoic acid, butyl 2-(acetyloxy) benzoate, 4-methoxy,2-(prop-2-en-yl) phenol, 3,6 dimethylbenzene-1, 2, 4 triyl triacetate and (4-ter butylphenyl)methanol.

Still in another embodiment of the present invention the process comprises a step of isolation of aromatic products and recycling of the Brönsted ionic liquid.

Still in another embodiment of the present invention recovery of the Brönsted ionic liquid comprises isolating the aromatic products; treating the aromatic products with THF to isolate THF soluble aromatic products subsequently treating the insoluble part of THF with water to selectively dissolve ionic liquids from other insoluble products followed by addition of HCl to obtain a mass and finally treating the mass with ethanol or methanol to isolate ionic liquid followed by evaporating ethanol to recover ionic liquid.

Still in another embodiment of the present invention the recovery of ionic liquid is carried out at ambient reaction conditions.

BRIEF DESCRIPTION OF THE DRAWINGS

FIG. 1 IR of different ionic liquids
FIG. 2 Synthesis of different Brönsted acidic ionic liquids (IL's)

DETAILED DESCRIPTION OF THE INVENTION

In view of above, the present invention provides a process for the depolymerization of lignin using acidic ionic liquids as catalysts to yield substituted phenolic compounds in high yields.

The present invention provides a process for the depolymerization of lignin comprising the steps of:
a. adding dealkaline lignin and Brönsted ionic liquid having —SO3H group to mixture of water and methanol to obtain a reaction mixture;
b. stirring the reaction mixture obtained in step (a) at a temperature in the range of 100 to 170° C. for a period of 0.5 to 6 hrs to afford the aromatic product in high yields.

The Brönsted ionic liquid having —SO$_3$H group is selected from the group consisting of (1-methyl-3-(3-sulfopropyl)-1H-imidazol-3-ium 4-methylbenzenesulfonate) [C$_3$SC$_1$IM] [PTSA], (1-methyl-3-(3-sulfopropyl)-1H-imidazol-3-ium hydrogensulfate) [C$_3$SC$_1$IM] [HSO$_4$], (1-methyl-3-(3-sulfopropyl)-1H-imidazol-3-ium chloride) [C$_3$SC$_1$IM] [Cl].

One preferable Brönsted ionic liquid having —SO$_3$H group according to the invention is (1-methyl-3-(3-sulfopropyl)-1H-imidazol-3-ium hydrogensulfate).

The lignin depolymerization is optionally be conducted in presence of acidic ionic liquid such as 1-butyl, 3-methyl imidazolium chloride.

The depolymerisation of lignin is carried out using the following conditions:

Lignin (0.5 g), [C$_3$SC$_1$IM] [HSO$_4$] (0.5 g), methanol and water (30 mL, ratio 5:1), 120° C., 1 h.

1st Run: 97% (THF soluble phenolic monomers)

In the second run due to loss of IL [C$_3$SC$_1$IM] [HSO$_4$] during recovery, for maintaining similar Lignin to catalyst ratio following condition are applied, Lignin (0.25 g), [C$_3$SC$_1$IM] [HSO$_4$] (0.25 g), methanol and water (15 mL, ratio 5:1), 120° C., 1 h.

2nd Run: 95% (THF soluble phenolic monomers)

The present invention provides a process for the synthesis of acidic ionic liquids in accordance with J. Mater. Chem., 2012, 22, 17140 comprising the steps of:
a. refluxing equimolar mixture of 1-methyl imidazole and 1,3-propane sultone in toluene for overnight to obtain a white precipitate (zwitter ion).
b. subjecting the white precipitate obtained in step (a) with equimolar solution of Brönsted acid without any solvent to afford the desired acidic ionic liquid.

The Brönsted acid used for the synthesis of acidic ionic liquids is selected from HCl, sulphuric acid or para-toluene sulfonic acid monohydrate.

The present invention provides the phenolic monomers formed by depolymerization of lignin are selected from the group consisting of 3,5 di ter-butyl,4-methylphenol, 2-ter-butyl,4-methylphenol, 4-acetyl benzoic acid, butyl 2-(acetyloxy) benzoate, 4-methoxy,2-(prop-2-en-yl) phenol, 3,6 dimethylbenzene-1,2, 4 triyl triacetate, and (4-ter butylphenyl)methanol as shown below:

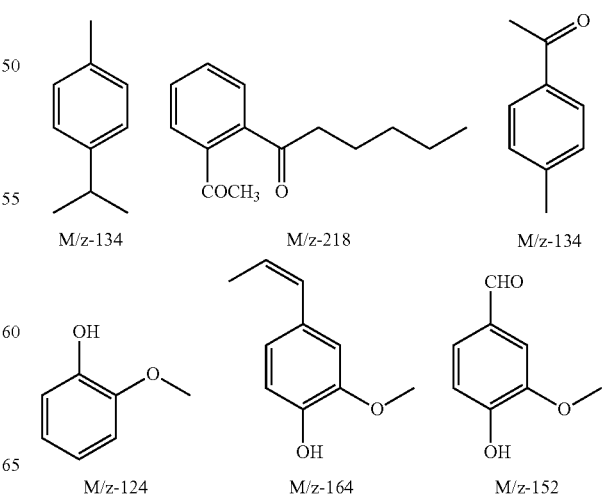

M/z-134    M/z-218    M/z-134

M/z-124    M/z-164    M/z-152

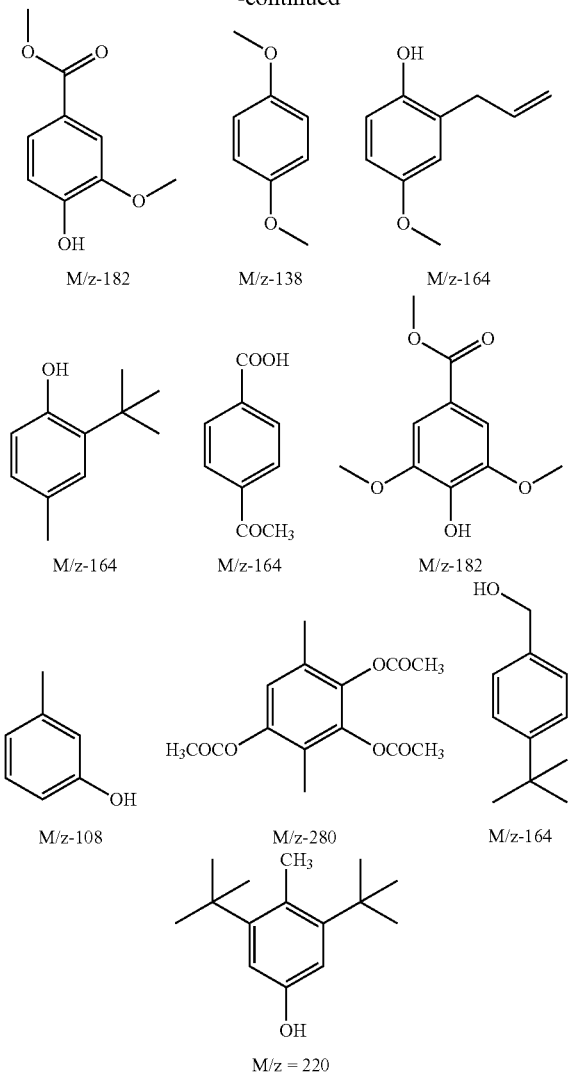

The invention provides a process for recovery of ionic liquids with Brönsted acidity which comprises the steps of:
a) removing the mixture of water and methanol from the reaction mixture to obtain solids; followed by treating the solids with THF to isolate THF soluble aromatic products;
b) treating the insoluble part of THF with water to selectively dissolve ionic liquids from other insoluble products followed by addition of HCl to form sodium contamination as NaCl which is also soluble in water along with ionic liquid
c) finally treated this mass with ethanol/methanol to isolate ionic liquid (soluble in solvent) from NaCl contamination (insoluble in solvent) followed by separation of solvent containing ionic liquid and then evaporating ethanol to recover ionic liquid.

The recovery may be carried out substantially under ambient conditions.

According to the above method, after the completion of the reaction, the solvent mix, water and methanol were removed by rotavap from the reaction mixture, to obtain solids. To this solid, THF was added to remove the organic compounds (obtained from lignin depolymerization). Since ionic liquid (IL) is not soluble in THF and stuck to round bottom flask, the THF was decanted and thus IL was separated from THF soluble organic compounds. To the insoluble part of THF (containing IL and other insoluble part) water was added to selectively dissolve ionic liquid and filtered the water soluble ionic liquid to separate the same from other organic compounds. To this solution, HCl was added to form NaCl from the Na contamination in IL (as lignin contains ppm level of Na). This solution was stirred at room temperature for 2 h. then rotavap was done to obtain IL with NaCl. To this semi viscous solid, ethanol/methanol was added to selectively isolate IL from NaCl as the same is not soluble in ethanol/methanol and filtered to separate the IL. The IL dissolved in ethanol then recovered after removing ethanol by rotavap and used for next reaction. The recovery of IL was confirmed by NMR, CHNS analysis, TGA etc.

Following are the examples given to further illustrate the invention and should not be construed to limit the scope of the present invention.

EXAMPLES

Example 1

Synthesis of Acidic Ionic Liquids

The synthesis of acidic ionic liquids is carried out in two step reaction. In the first step, equimolar mixture of 1-methyl imidazole and 1,3-propane sultone refluxed in toluene for overnight 16 hours at 115° C. giving white precipitate (zwitter ion). In the second step reaction the white precipitate is reacted with equimolar solution of HCl without any solvent giving acidic ionic liquid 1-methyl-3-(3-sulfopropyl)-1H-imidazol-3-ium chloride for 16 hours at 105° C.). Similarly other acidic ionic liquids are synthesized by reaction of zwitter ion with equimolar solution of sulphuric acid and para-toluene sulfonic acid monohydrate.

Example 2

Characterization of Catalyst

A) (1-methyl-3-(3-sulfopropyl)-1H-imidazol-3-ium 4-methylbenzenesulfonate)

$^1$HNMR (200 MHz, D$_2$O) δ 8.59 (s, 1H), 7.55 (d, 2H), 7.36 (s, 1H), 7.30 (s, 1H), 7.27 (d, 2H), 4.11 (t, 2H), 3.76 (s, 3H), 2.83 (t, 2H) 2.28 (s, 3H), 1.90 (m, 2H)
$^{13}$CNMR 142.42, 139.43, 136.09, 129.40, 125.31, 123.72, 122.14, 47.69, 47.17, 35.66, 25.05, 20.44

Microanalysis: the approximate % of element by microanalysis is C (43), H (5.3), N (7.5) and S (15).

B) (1-methyl-3-(3-sulfopropyl)-1H-imidazol-3-ium hydrogensulfate) [C$_3$SC$_1$IM] [HSO$_4$]

$^1$HNMR (200 MHz, D2O) δ 8.66 (s, 1H), 7.42 (s, 1H), 7.35 (s, 1H), 4.26 (t, 2H), 3.79 (s, 3H), 2.82 (t, 2H), 2.21 (m, 2H)
$^{13}$CNMR 136.16, 123.74, 122, 47.69, 47.19, 35.66, 25

Microanalysis: the approximate % of element by microanalysis is C (30.56), H (7.31), N (11.63) and S (23.89)

C) 1-methyl-3-(3-sulfopropyl)-1H-imidazol-3-ium chloride $^1$HNMR (200 MHz, D$_2$O) δ 8.63 (s, 1H), 7.40 (s, 1H), 7.32 (s, 1H), 4.24 (t, 2H), 3.77 (s, 3H), 2.80 (t, 2H), 2.19 (m, 2H)

$^{13}$CNMR 136.19, 123.76, 122.18, 47.72, 47.18, 35.7, 25.08

Microanalysis: the approximate % of element by microanalysis is C (35.10), H (6.02), N (13.16) and S (14.25)

D) 1-butyl, 3-methyl imidazolium chloride $^1$HNMR (200 MHz, D$_2$O) δ 8.82 (s, 1H), 7.67 (s, 1H), 7.61 (s, 1H), 4.35 (t, 3H), 4 (s, 3H), 1.91 (m, 2H), 1.40 (m, 2H), 0.94 (t, 3H)
$^{13}$CNMR 123.76, 122.18, 49.32, 35.7, 31.2, 19.12, and 12.34

Microanalysis: the approximate % of element by microanalysis, is C (55), H (9) and N (16)

Example 3

Depolymerisation of Lignin Using Following Conditions

Dealkaline Lignin (0.5 g), [C$_3$SC$_1$IM] [HSO$_4$] (0.5 g) taken in methanol and water (30 mL, ratio 5:1) and stirred the reaction mixture at a temperature of 120° C. for 1 h and the reaction products are analyzed for the THF soluble phenolic monomers.

Yield: 97% (THF soluble phenolic monomers).

| S.N. | Name of compound | m/z |
|---|---|---|
| 1 | p-cymene | 134 |
| 2 | 1-(2-acetylphenyl)hexan-1-one | 218 |
| 3 | 1-(p-tolyl) ethan-1-one | 134 |
| 4 | 2-methoxyphenol | 124 |
| 5 | (Z)-2-methoxy-4-(prop-1-en-1-yl)phenol | 164 |
| 6 | 4-hydroxy-3-methoxybenzaldehyde | 152 |
| 7 | methyl 4-hydroxy-3-methoxybenzoate | 182 |
| 8 | 1,4-dimethoxybenzene | 138 |
| 9 | 2-allyl-4-methoxyphenol | 164 |
| 10 | 2-(tert-butyl)-4-methylphenol | 164 |
| 11 | 4-acetylbenzoic acid | 164 |
| 12 | methyl 4-hydroxy-3,5-dimethoxybenzoate | 182 |
| 13 | m-cresol | 108 |
| 14 | 4-(methoxycarbonyl)-3,6-dimethyl-1,2-phenylene diacetate | 280 |
| 15 | (4-(tert-butyl)phenyl)methanol | 164 |
| 16 | 3,5-di-tert-butyl-4-methylphenol | 220 |

Catalytic reaction results are summarized in the following tables.

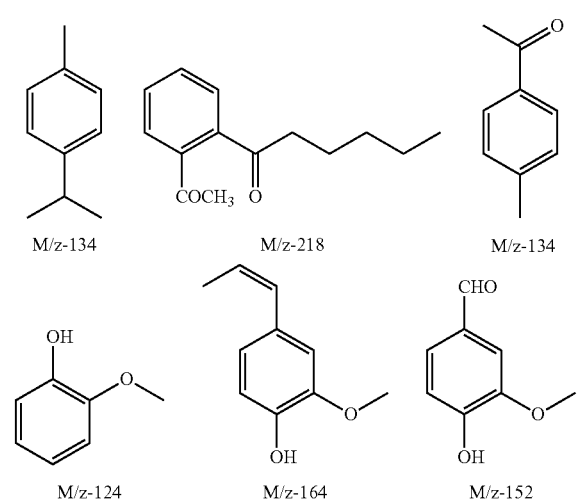

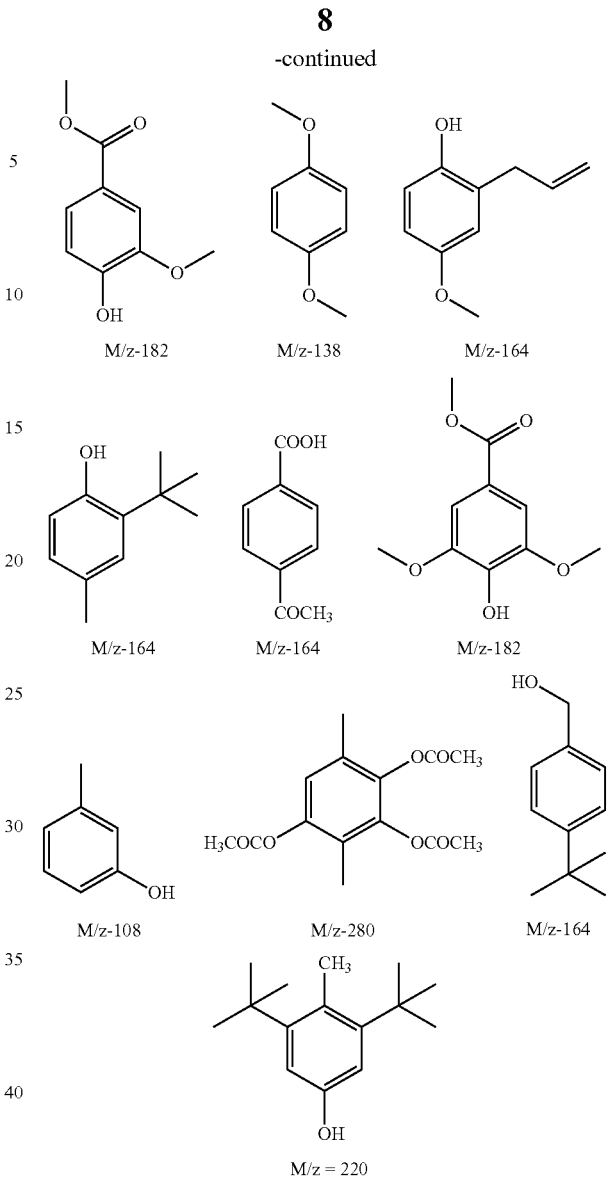

Solvent Ratio Study:

Methanol to water ratio was changed and the results are presented below in table 1

TABLE 1

| Methanol:water | THF soluble products yield (%) |
|---|---|
| 0:1 | 9 |
| 1:5 | 27 |
| 1:1 | 33 |
| 5:1 | 97 |

Reaction condition, Lignin (0.5 g), [C$_3$SC$_1$IM] [HSO$_4$] (0.5 g), methanol+water (30 mL), 120° C., 1 h.

From the above, it is evident that the methanol/water ratio of 5 gives better product yield.

The effect of acidic ionic liquid on depolymerisation of lignin is shown in table 2.

TABLE 2

| Sr. No. | Catalyst | Temperature, °C | Time, h | Yield, % THF soluble | Yield, % EtOAc soluble | Yield, % Mix solvent soluble |
|---|---|---|---|---|---|---|
| 1 | Without catalyst | 150 | 1 | 0.5 | 1.2 | 2.5 |
| 2 | [C$_3$SC$_1$IM][PTSA] | 150 | 1 | 18 | 15 | 17 |

Lignin (0.2 g), catalyst (0.05 g), solvent (water+MeOH=2+10 mL)

Mix solvent: THF+EtOAc

From the above, it is evident that the use of ionic liquid improves the yield of phenolic monomers.

The effect of catalyst quantity on the depolymerisation of lignin is shown in table 3.

TABLE 3

| Sr. No. | Catalyst | Catalyst wt., g | Time, h | Yield, % THF soluble | Yield, % EtOAc soluble | Yield, % Mix solvent soluble |
|---|---|---|---|---|---|---|
| 1 | Without catalyst | 0 | 1 | 0.5 | 1.2 | 2.5 |
| 2 | [C$_3$SC$_1$IM][PTSA] | 0.05 | 1 | 18 | 15 | 17 |
| 3 | [C$_3$SC$_1$IM][PTSA] | 0.20 | 1 | 69 | 68 | 75 |

Lignin (0.2 g), temperature (150° C.), solvent (water+MeOH=2+10 mL)

Mix solvent: THF+EtOAc

Form the above it is evident that the ratio of lignin to catalyst in 1:1 gives better yields.

The effect of time on depolymerisation of lignin is depicted in table 4.

TABLE 4

| Sr. No. | Catalyst | Temperature, °C | Time, h | Yield, % THF soluble | Yield, % EtOAc soluble | Yield, % Mix solvent soluble |
|---|---|---|---|---|---|---|
| 1 | Without catalyst | 150 | 1 | 0.5 | 1.2 | 2.5 |
| 2 | Without catalyst | 150 | 2 | 6.0 | 4.0 | 5.0 |
| 3 | [C$_3$SC$_1$IM][PTSA] | 150 | 1 | 69 | 68 | 75 |
| 4 | [C$_3$SC$_1$IM][PTSA] | 150 | 2 | 78 | 55 | 83 |
| 5 | [C$_3$SC$_1$IM][PTSA] | 150 | 6 | 61 | 60 | 61 |

Lignin (0.2 g), catalyst (0.2 g), solvent (water+MeOH=2+10 mL)

Mix solvent: THF+EtOAc

From the above table, it is clear that the reaction period of 2 hrs is sufficient to yield better results when compared to extended reaction period of 6 hrs.

The reduction in the yield may be attributed to a possible decomposition of the products or repolymerisation of products.

The effect of reaction temperature on depolymerisation of lignin is shown in table 5.

TABLE 5

| Sr. No. | Catalyst | Temperature, °C | Time, h | Yield, % THF soluble | Yield, % EtOAc soluble | Yield, % Mix solvent soluble |
|---|---|---|---|---|---|---|
| 1 | [C$_3$SC$_1$IM][PTSA] | 100 | 2 | 54 | 53 | 60 |
| 2 | [C$_3$SC$_1$IM][PTSA] | 120 | 2 | 60 | 59 | 64 |
| 3 | [C$_3$SC$_1$IM][PTSA] | 150 | 2 | 78 | 55 | 83 |

Lignin (0.2 g), catalyst (0.2 g), solvent (water+MeOH=2+10 mL)

Mix solvent: THF+EtOAc As is evident from the above study, although the reaction proceeds smoothly even at a temperature of 100° C. gave up to 60% yield, however, the yields are improved up to 83% with increase in temperature.

The effect of IL's on depolymerisation of lignin is shown in table 6.

TABLE 6

| Sr. No. | Catalyst | Temperature, °C | Time, h | Yield, % THF soluble | Yield, % EtOAc soluble | Yield, % Mix solvent soluble |
|---|---|---|---|---|---|---|
| 1 | [C$_3$SC$_1$IM][PTSA] | 150 | 1 | 69 | 68 | 75 |
| 2 | [C$_3$SC$_1$IM][HSO$_4$] | 150 | 1 | 97 | 53 | 83 |
| 3 | [C$_3$SC$_1$IM][Cl] | 150 | 1 | 54 | 38 | 50 |

Lignin (0.2 g), Catalyst (0.2 g), solvent (water+MeOH=2+10 mL)

Mix solvent: THF+EtOAc

From the above table it is evident that although the reaction proceeds smoothly with different anions of (1-methyl-3-(3-sulfopropyl)-1H-imidazol-3-ium, however, the best results are achieved with (1-methyl-3-(3-sulfopropyl)-1H-imidazol-3-ium with (HSO$_4$) anion. The phenolic monomers with an yield of 97% are obtained with the use of Brönsted ionic liquid (having —SO$_3$H group), i.e., (1-methyl-3-(3-sulfopropyl)-1H-imidazol-3-ium with SO$_3$H group.

The catalytic reaction mixture was analyzed by GC and GCMS to assess the percent yield of phenolic monomer products.

The Characterization of acidic Ionic Liquids was done with $^1$H and $^{13}$C NMR, CHNS analysis, IR and TGA.

Example 4

The recycled catalyst was used in the second run. Due to loss of IL [C$_3$SC$_1$IM] [HSO$_4$] during recovery process, for maintaining similar Lignin to catalyst ratio an additional amount of Lignin (0.25 g) and the IL catalyst [C$_3$SC$_1$IM] [HSO$_4$] (0.25 g) along with methanol and water (15 mL) to maintain the ratio of 5:1. The reaction mass was stirred at a temperature of 120° C. for 1 h and the reaction mass was analyzed for THF soluble fraction.

Yield: 76% (THF soluble phenolic monomers)

Example 5

Method for Recycling of Catalyst

After the reaction, from the reaction mixture, solvent (water+methanol) was removed by rotavap to obtain solids. To this solid, THF was added to remove any organic compounds (obtained from lignin depolymerization). Since ionic liquid (IL) is not soluble in THF and very sticky it was stuck to round bottom flask. Afterwards THF was decanted and thus IL was separated from THF soluble. To the insoluble part of THF (containing IL and other insoluble part) water was added. IL dissolves in water and other organic compounds are not. After filtration water soluble IL was separated out. To this solution HCl was added to form NaCl since Na was a contamination in IL (as lignin contains ppm level of Na). This solution was stirred at room temperature for 2 h. then rotavap was done to obtain IL with NaCl. To this semi viscous solid, ethanol was added. Since NaCl is not soluble in ethanol but IL is soluble in ethanol, separation of NaCl and IL was done using filtration. The IL dissolved in ethanol then recovered after removing ethanol by rotavap. This IL was used for next reaction. The recovery of IL was confirmed by NMR, CHNS analysis, IR, TGA etc.

Advantages of Invention a. Depolymerization of lignin compounds under mild conditions b. Aromatic monomers having molecular weight <300 obtained c. Yields monomers formation is up to 97%.

We claim:

1. A process for the depolymerization of lignin to obtain aromatic products comprising the steps of:
   a. adding dealkaline lignin and Brönsted ionic liquid having —SO$_3$H group in the range of 1:0.25 to 1:1 to a mixture of water and methanol wherein the ratio of methanol to water is in the range of 0:1 to 5:1 to obtain a reaction mixture;
   b. stirring the reaction mixture obtained in step (a) at a temperature range of 100 to 170° C. for a period of 0.5 to 6 hrs to afford the aromatic products with 95-97% yield and a mass balance of >90%.

2. The process according to claim 1, wherein the Brönsted ionic liquid having —SO$_3$H group used in step (a) is selected from the group consisting of (1-methyl-3-(3-sulfopropyl)-1H-imidazol-3-ium 4-methylbenzenesulfonate), (1-methyl-3-(3-sulfopropyl)-1H-imidazol-3-ium hydrogensulfate), and (1-methyl-3-(3-sulfopropyl)-1H-imidazol-3-ium chloride).

3. The process according to claim 2, wherein the Brönsted ionic liquid having —SO$_3$H group used is (1-methyl-3-(3-sulfopropyl)-1H-imidazol-3-ium hydrogensulfate).

4. The process according to claim 1, wherein the aromatic products are phenolic monomers obtained with m/z in the range of 100 to 300.

5. The process according to claim 4, wherein the phenolic monomers are THF soluble.

6. The process according to claim 4, wherein the phenolic monomers are selected from the group consisting of 3,5 di ter-butyl,4-methylphenol, 2-ter-butyl, 4-methylphenol, 4-acetyl benzoic acid, butyl 2-(acetyloxy) benzoate, 4-methoxy,2-(prop-2-en-yl) phenol, 3,6 dimethylbenzene-1, 2,4 triyl triacetate, and (4-ter butylphenyl)methanol.

7. The process according to claim 1, wherein the process comprises a step of isolation of aromatic products and recovery of the Brönsted ionic liquid.

8. The process according to claim 7, wherein recovery of the Brönsted ionic liquid comprises isolating the aromatic products; treating the aromatic products with THF to isolate THF soluble aromatic products subsequently treating the insoluble part of THF with water to selectively dissolve ionic liquids from other insoluble products followed by addition of HCl to obtain a mass and finally treating the mass with ethanol or methanol to isolate ionic liquid followed by evaporating ethanol to recover ionic liquid.

9. The process according to claim 8, wherein the recovery of ionic liquid is carried out at ambient reaction conditions.

* * * * *